(12) United States Patent  
Wen

(10) Patent No.: US 10,137,092 B2  
(45) Date of Patent: Nov. 27, 2018

(54) DOUBLE-LAYER TABLET AND PREPARATION METHOD THEREOF

(71) Applicant: Xiaoguang Wen, Guangzhou (CN)

(72) Inventor: Xiaoguang Wen, Guangzhou (CN)

( * ) Notice: Subject to any disclaimer, the term of this patent is extended or adjusted under 35 U.S.C. 154(b) by 0 days.

(21) Appl. No.: 15/107,892

(22) PCT Filed: Dec. 19, 2014

(86) PCT No.: PCT/CN2014/094367  
§ 371 (c)(1),  
(2) Date: Jun. 23, 2016

(87) PCT Pub. No.: WO2015/096668  
PCT Pub. Date: Jul. 2, 2015

(65) Prior Publication Data  
US 2016/0317449 A1    Nov. 3, 2016

(30) Foreign Application Priority Data

Dec. 23, 2013  (CN) .......................... 2013 1 0716482  
Dec. 23, 2013  (CN) .......................... 2013 1 0717968  
Dec. 23, 2013  (CN) .......................... 2013 1 0718529

(51) Int. Cl.  
*A61K 9/20*        (2006.01)  
*A61K 31/437*    (2006.01)  
(Continued)

(52) U.S. Cl.  
CPC .......... *A61K 9/2086* (2013.01); *A61K 9/2072* (2013.01); *A61K 9/2095* (2013.01);  
(Continued)

(58) Field of Classification Search  
CPC .. A61K 9/2086; A61K 9/2072; A61K 9/2095; A61K 31/437; A61K 31/4985; A61K 31/519  
See application file for complete search history.

(56) References Cited

U.S. PATENT DOCUMENTS 3,840,631 A * 10/1974 Alexander ................ A61J 3/10  
                                       264/113  
7,611,722 B2 * 11/2009 Lerner ................... A61J 3/005  
                                       424/400  
(Continued)

FOREIGN PATENT DOCUMENTS

CN          101212136      * 12/2009             A61K 9/36  
CN          102085196 A     6/2011  
(Continued)

OTHER PUBLICATIONS

CN102600097 Machine Translation (2017).*  
(Continued)

*Primary Examiner* — Sean M Basquill  
(74) *Attorney, Agent, or Firm* — Gokalp Bayramoglu

(57) ABSTRACT

The invention discloses a double-layer tablet, wherein one layer has hole in which the ingredients of the other layer are filled; the number of said hole is 1-3, the diameters of the holes are 1-10 mm. Each layer of the double-layer tablet includes the active ingredients and the adjuvant materials and can be the rapid-release layer or sustained-release layer respectively. The preparation method: Preparing respectively a component I and a component II, both of them containing the active ingredients and the pharmaceutical excipients, and preparing the tablet having holes from component I; Forming the double-layer tablet composed of the component I layer and the component II layer after pressing said tablet having holes with the component II together; and filling the component II into the holes during compressing. It is proved by tests that the double-layer table in the invention is featured with high physical stability, hard breaking during transportation and storage, approximately constant release of medicine and usefulness of keeping stable plasma concentration of the medicine in the patient; thus, the (Continued)

effectiveness and safety of the medicine taken by the patient are improved greatly.

14 Claims, 6 Drawing Sheets

(51) Int. Cl.
*A61K 31/4985* (2006.01)
*A61K 31/519* (2006.01)

(52) U.S. Cl.
CPC ........ *A61K 31/437* (2013.01); *A61K 31/4985* (2013.01); *A61K 31/519* (2013.01)

(56) References Cited

U.S. PATENT DOCUMENTS 7,807,197 B2 * 10/2010 Lee ...................... A61K 9/2072
424/467
2016/0317449 A1    11/2016   Wen

FOREIGN PATENT DOCUMENTS

| CN | 102600097 | * | 7/2012 | ............... A61K 9/24 |
| CN | 102600097 A | | 7/2012 | |
| CN | 103655505 B | | 3/2014 | |
| CN | 103690503 B | | 4/2014 | |
| CN | 103690505 B | | 4/2014 | |
| EP | 2 682 110 A1 | | 1/2014 | |
| EP | 3 087 980 A1 | | 11/2016 | |
| WO | WO 2012/118180 A1 | | 9/2012 | |

OTHER PUBLICATIONS

Erica Sundy & Michael Paul Danckwertz, A Novel Compression-Coated Doughnut-Shaped Tablet Design for Zero-Order Sustained Release, 22 Eur. J Pharma. Sci. 477 (2004).*
Fridrun Podczeck, Theoretical and Experimental Investigations into the Delamination Tendencies of Bilayer Tablets, 408 Intl. J Pharmaceutics, 102, 102-03 (Year: 2011).*
CN101212136 MA achine Translation (Year: 2009).*
International Preliminary Report on Patentability for PCT/CN2014/094367, dated Jun. 28, 2016, 13 pages (Including English translation).
International Search Report for PCT/CN2014/094367, dated Mar. 25, 2015, 4 pages (Including English translation).
Yang et al., "Research progress for bipolar drug-releasing system of bilayer tablets," (2011) Chin Pharm J 46(23):1777-1780 (Including English translation).

* cited by examiner

DOUBLE-LAYER TABLET AND PREPARATION METHOD THEREOF

This application is a U.S. National Phase of International Patent Application No. PCT/CN2014/094367, filed Dec. 19, 2014, which claims benefit of priority to Chinese Patent Application No. 201310717968.1, filed Dec. 23, 2013, Chinese Patent Application No. 201310716482.6, filed Dec. 23, 2013, and Chinese Patent Application No. 201310718529.2, filed Dec. 23, 2013, the disclosures of which applications are incorporated by reference herein in their entireties for all purposes.

The priority request is proposed in this application in allusion to following three patent applications in China:
"A method of double-layer tablet" with application No.: 201310717968.1
"An analgesic double-layer controlled-release tablet and a preparation method thereof" with application No.: 201310716482.6
"A hypnotic double-layer controlled-release tablet and a preparation method thereof" with application No.: 201310718529.2

The above-mentioned three prior applications were applied on Dec. 23, 2013.

TECHNICAL FIELD

The invention refers to the field of medicinal preparation, specifically a novel double-layer tablet and a preparation method thereof.

BACKGROUND TECHNOLOGY

A double-layer tablet is a double-phase medicine-release system having a double-layer structure, which not only can achieve the ideal pharmacokinetic behavior by combining two medicines together or combining identical medicine in different release modes together, but improve the stability of the medicines having incompatibility and give the special functions to the tablet.

In preparation of the double-layer tablet, to ensure the medicine of double-layer tablet has the stable structure during the shelf life is the most demanding and practical technology in pharmaceuticals industry.

The double-layer tablet in the prior art includes two layers of tablets which are adhered to each and the preparation method thereof is to press the two layers of tablets one by one usually, for example, mix the medicinal active ingredients and the pharmaceutical excipients of one layer of the double-layer tablet and press the mixture into one layer of tablet; then prepare the double-layer after pressing this tablet with the medicinal active ingredients and the pharmaceutical excipients of the other layer of tablet together.

The double-layer tablet of the prior art is featured with poor physical stability, easy breaking and separation of the two layers; and the preparation may be cracked, etc. during transportation and storage as a result of difference of dilatation coefficients among the different pharmaceutical excipients because different pharmaceutical excipients are applied to the two layers of tablets usually.

Therefore, it is necessary to improve the physical stability of the double-layer tablet and ensure integrity of the preparation during transportation and storage.

CONTENTS OF THE INVENTION

The invention is to provide a double-layer tablet, which featured with high physical stability, not easy to broken during transportation and storage, approximately constant release of medicine and capability of improving effectiveness and safety of the patient taking the medicine.

The invention achieves the purpose of the above-mentioned invention by designing the double-layer tablet having a new structure, wherein the technical solution is as follows:

The double-layer tablet refers to a double-layer medicine-release mode, which is formed by combining two layers of tablets together, wherein one layer of tablet has hole. Moreover, said hole has the ingredients of the other layer of tablet when the preparation is prepared.

Each layer of said double-layer tablet includes the active ingredients and pharmaceutical excipients, wherein the active ingredients in each layer can be one or two or more than two active ingredients. The active ingredients in two layers of the double-layer tablet can be the same or different from each other.

Each layer of the double-layer tablet can be the quick release layer or the sustained-release layer, respectively.

The number of said holes is 1-3, preferably 1.
The diameters of said holes are 1-10 mm, preferably 2-6 mm.

Said double-layer tablet can be coated, etc. by using the conventional method in this field in accordance with the actual need.

A method of preparing said double-layer tablet includes the steps of
1) Preparing respectively a component I and a component II, both of them containing the active ingredients and the pharmaceutical excipients, and said component I and the component II are granules or powder;
2) Implementing the first tabletting: preparing the tablet having hole from component I (also called tablet I below);
3) Implementing the second tabletting: forming the double-layer tablet composed of the component I layer and the component II layer after pressing said tablet having holes with the component II together; and filling the component II into the holes during compressing.

Said hole can be formed by using a compressing mould having holes, or punching the tablets after compressing Moreover, in one embodiment of the invention, the tablet II with hole is formed from the component I by using an annular punch.

As for the advantages of the invention, the component I layer of the double-layer tablet has holes; the double-layer tablet acquired is very firm and cannot be separated during transportation and storage because the component II is filled in the holes of the tablet I. See FIG. 1-3 for structure.

The preparation method of the double-layer tablet in the invention is applicable for preparation of kinds of double-layer tablet. Further, the technicians in this field can select all kinds of conventional pharmaceutical excipients in accordance with actual need.

The pharmaceutical excipients is one or more selected from sustained-release material, filler, disintegrating agent, lubricant, binder and glidant. The sustained-release material is one or more preferably selected from hydroxylpropylmethyl-cellose, ethyecellulose and hydroxy propyl cellulose; the filler is one or more preferably selected from lactose, pregelatinized starch and microcrystalline cellulose; the disintegrating agent is one or more preferably selected from sodium carboxymethyl cellulose, sodium carboxymethyl starch and polyvinylpolypyrrolidone; the lubricant is one or more preferably selected from stearic acid, magnesium stearate and talcum powder; the binder is one or more preferably selected from polyvidone, hydroxy propyl cellulose and hydroxylpropylmethyl-cellose; and the glidant is superfine silica powder preferably.

The component I in the invention preferably includes following ingredients with percentages by weight:

| Medicine | 1-60% |
| Sustained-release material | 0-25% |
| Disintegrating agent | 0-6% |
| Binder | 0~5% |
| Filler | 5-60% |
| Lubricant | 0.1-0.5% |
| Glidant | 0.1-0.5% |

The granules II in the invention preferably include following ingredients with percentages by weight:

| Medicine | 1~90% |
| Sustained-release material | 0~40% |
| Disintegrating agent | 0~6% |
| Binder | 0~5% |
| Filler | 5~90% |
| Lubricant | 0.1~0.5% |
| Glidant | 0.1~0.5% |

The double-layer table of the invention also includes the coating preferably, wherein the coating comprises following components with percentage:

| Hydroxypropylmethyl-cellose E5 | 40-60% |
| Polysorbate 80 | 20-35% |
| Talcum powder | 6-12% |
| Titanium dioxide | 2-6% |

The following refers to an example of the double-layer tablet prepared in accordance with the solution of the invention and combining with the analgesic quick release/sustained release:

A analgesic double-layer controlled-release tablet comprises a quick release layer and a sustained-release layer; both quick release layer and sustained-release layer comprise the active ingredients having analgesic effect and pharmaceutical excipients, wherein said sustained-release layer has holes in which the granules of medicine of the quick release layer are filled; the diameters of the holes are 2-6 mm.

Said active ingredients having analgesic effect refer to one or more selected from aspirin, magnesium salicylate, sodium salicylate, choline magnesium trisalicylate, diflunisal, salsalate, ibuprofen, indometacin, flurbiprofen, phenoxy ibuprofen naproxen, nabumnetone, piroxicam, phenylbutazone, diclofenac sodium, fenoprofen, ketoprofen, ketorolac, tetraclofenamic acid, sulindac, tolmetin, anisodamine, and the derivatives of the above-mentioned compounds; said quick release layer and said sustained-release layer include the identical or different active ingredients; said pharmaceutical excipients refer to one or more selected from filler, disintegrating agent, lubricant, binder and glidant.

All kinds of pharmaceutical excipients listed below can be selected, but are not limited to the scope the invention. Actually, all kinds of pharmaceutical excipients used in the invention can be the pharmaceutical excipients which are used by the technicians in this field generally in accordance actual need, for example, said filler ers to one or more selected from lactose monohydrate, pregelatinized starch and microcrystalline cellulose; said disintegrating agent refers to one or more selected from sodium carboxymethyl cellulose, croscarmellose sodium, sodium carboxymethyl starch and polyvinylpolypyrrolidone; said lubricant is one or more selected from stearic acid, magnesium stearate and talcum powder; said binder is one or more selected from polyvidone, hydroxy propyl cellulose and hydroxypropylmethyl-cellose; and said glidant is silicon dioxide. Moreover, the sustained-release layer in the analgesic double-layer tablet also comprises the sustained-release material.

Said sustained-release material is one or more selected from hydroxypropylmethyl-cellose, ethylcellulose and hydroxy propyl cellulose; and said sustained-release layer comprises the following component by weight:

| Analgesic medicine | 40-60% |
| Sustained-release material | 25~35% |
| Filler | 13~24% |
| Lubricant | 0.5 or 1% |
| Glidant | 0.5 or 1%; |

Said quick release layer and the quick release granule comprise the following component by weight:

| Analgesic medicine | 30-60% |
| Disintegrating agent | 3~6% |
| Filler | 30~60.5% |
| Binder | 0~5% |
| Lubricant | 0.5 or 1% |
| Glidant | 0.5 or 1%. |

Said double-layer controlled-release tablet also comprises the coating which includes the following component by weight:

| Hydroxypropylmethyl-cellose E5 | 30% |
| Polysorbate 80 | 14% |
| Talcum powder | 5% |
| Titanium dioxide | 2% |
| Water | Appropriate |

A method of preparing the analgesic double-layer controlled-release layer comprises the steps of:
1) Preparing the sustained-release granules after mixing the analgesic medicine, the sustained-release material and the pharmaceutical excipients; and preparing the quick release granules after mixing the analgesic medicine and the pharmaceutical excipients;
2) Pressing the sustained-release granules into the sustained-release layer having holes, and putting the sustained-release layer into a punching die of a tablet press; implementing the second tabletting after filling the quick release granules to form the double-layer tablet composed of the quick release layer and the sustained-release layer, wherein the quick release granules are filled in the holes of the sustained-release layer.

3) Implementing coating.

The following refers to one example of the double-layer tablet prepared in accordance with the solution of the invention and combining with the hypnotic quick release/ sustained release:

Said hypnotic medicine is one of zolpidem, zaleplon, zopiclone, triazolam, midazolam, flurazepam, diazepam, chlordiazepoxide, nitrazepam, estazolam, alprazolam or lorazepam, and the derivatives of the above-mentioned compounds; said sustained-release material is one or more selected from hydroxypropylmethyl-cellose, ethyecellulose and hydroxy propyl cellulose; and said pharmaceutical excipients is one or more selected from filler, disintegrating agent, lubricant, binder and glidant.

Said filler is one or more selected from lactose monohydrate, lactose, pregelatinized starch and microcrystalline cellulose; said disintegrating agent refers to one or more selected from sodium carboxymethyl cellulose, croscarmellose sodium, sodium carboxymethyl starch and polyvinylpolypyrrolidone; said lubricant is one or more selected from stearic acid, magnesium stearate and talcum powder; said binder is one or more selected from polyvidone, hydroxy propyl cellulose and hydroxypropylmethyl-cellose; and said glidant is silicon dioxide.

Said sustained-release layer in the double-layer controlled-release tablet comprises following components by weight:

| | |
|---|---|
| Hypnotic medicine | 8-12% |
| Sustained-release material | 30-35% |
| Filler | 52-61% |
| Lubricant | 0.5 or 1% |
| Glidant | 0.5 or 1%; |

Said quick release layer and the quick release granules comprise following components by weight:

| | |
|---|---|
| Hypnotic medicine | 5~10% |
| Disintegrating agent | 2~6% |
| Filler | 80.5~91% |
| Binder | 0~5% |
| Lubricant | 0.5 or 1% |
| Glidant | 0.5 or 1% |

The method of preparing said hypnotic double-layer controlled-release tablet comprises steps of 1) Preparing the sustained-release granules after mixing the hypnotic medicine, the sustained-release material and the pharmaceutical excipients; and preparing the quick release granules after mixing the hypnotic medicine and the pharmaceutical excipients;

2) Pressing the sustained-release granules into the sustained-release layer having holes, and putting the sustained-release layer into the punching die of the tablet press; implementing the second tabletting after filling the quick release granules to form the double-layer tablet composed of the quick release layer and the sustained-release layer, wherein the quick release granules are filled the holes of the sustained-release layer.

3) Implementing coating, wherein the formula of the coating layer and the preparation method are the same as those of the analgesic double-layer controlled-release tablet.

The invention has the technical effects as follows:

1) Nice Physical Stability

One layer of the double-layer tablet has holes which will be filled by the components of the other layer during preparation of tablets; therefore, the two layers of tablets are combined together tightly, and cannot be separated easily during storage and transportation.

2) Effectiveness and Safety of the Medicine Improved

It is detected by leaching test that the time limit of disintegration of the double-layer controlled-release tablet is 10-30 s; the sustained-release layer shows the zero order release mode, that is, approximately constant release of medicine, which can facilitate implementation of keeping the stable plasma concentration of the medicine in patient; thus, the effectiveness and the safety of the medicine taken by the patient are improved greatly.

DESCRIPTION OF FIGURES

In FIG. 1, FIG. 2 and FIG. 3, 1 indicates the tablet I, 2 indicates the tablet II, and 3 indicates the hole.

IMPLEMENTATIONS

Figure 1:
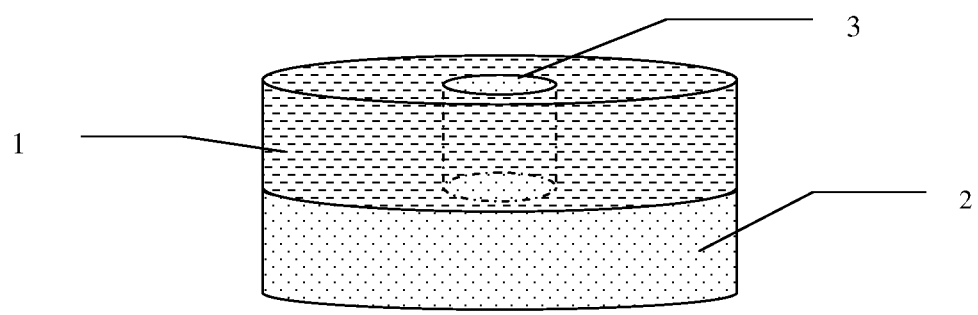
FIG. 1 is the structure diagram of a double-layer tablet having one hole.
Figure 2:
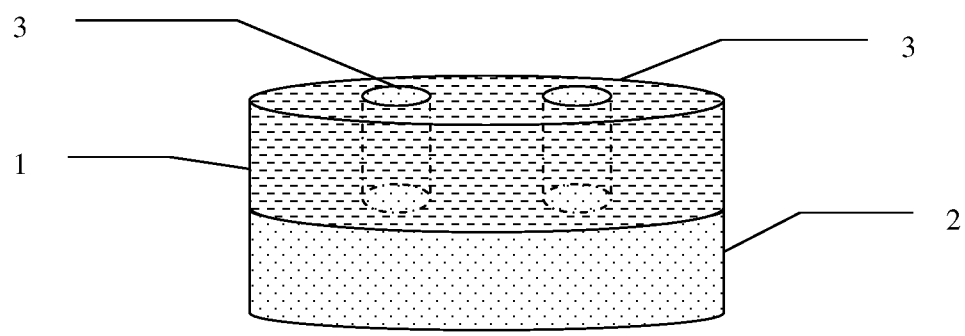
FIG. 2 is the structure diagram of the double-layer tablet having two holes.
Figure 3:
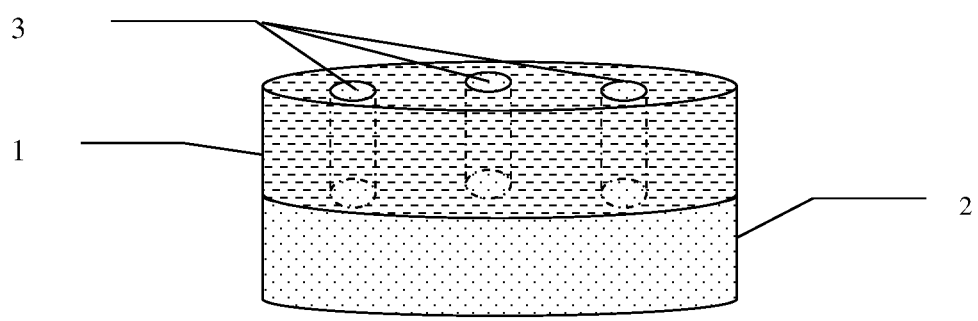
FIG. 3 is the structure diagram of the double-layer tablet having three holes.

The double-layer controlled-release tablet in analgesic embodiments 1-5 is composed of a quick release layer and a sustained-release layer. See Table 1 below for two layers of granules for tabletting the double-layer tablets:

TABLE 1

Prescriptions of the double-layer controlled-release tablet in all embodiments (1000 tablets, g)

| Component | Embodiment 1 | Embodiment 2 | Embodiment 3 | Embodiment 4 | Embodiment 5 |
|---|---|---|---|---|---|
| Sustained-release granules | | | | | |
| Ibuprofen | 250 | 250 | | 300 | 200 |
| Ketoprofen | | | | | |
| Naproxen | | | 300 | | |
| Hydroxypropylmethyl-cellulose K100lv | 50 | 100 | 0 | 25 | 150 |
| Hydroxypropylmethyl-cellulose K4M | 100 | 50 | 125 | 100 | 25 |
| Lactose monohydrate | 95 | 95 | 65 | 70 | 120 |
| Silicon dioxide | 2.5 | 2.5 | 5 | 2.5 | 2.5 |
| Magnesium stearate | 2.5 | 2.5 | 5 | 2.5 | 2.5 |
| Total of sustained-release part | 500 | 500 | 500 | 500 | 500 |
| Sustained-release granules | | | | | |
| Acetaminophen | | | | | 150 |
| Ibuprofen | | | | 150 | |
| Ketoprofen | 75 | | | | |
| Naproxen | | 100 | 150 | | |
| Lactose | 87.5 | 62.5 | 50 | 25 | 75 |
| Microcrystalline cellulose | 63.75 | 60 | 40 | 50 | 0 |
| Polyvidone | 8.75 | 0 | 0 | 0 | 10 |
| Hydroxypropyl-cellulose-HF | 0 | 12.5 | 0 | 7.5 | 0 |
| Croscarmellose sodium | 10 | 10 | 7.5 | 15 | 12.5 |
| Silicon dioxide | 2.5 | 2.5 | 1.25 | 1.25 | 1.25 |
| Magnesium stearate | 2.5 | 2.5 | 1.25 | 1.25 | 1.25 |
| Total of quick release part | 250 | 250 | 250 | 250 | 250 |

The coating can be applied to said double-layer tablet and the coating comprises following components:

| | |
|---|---|
| Hydroxypropylmethyl-cellulose E5 | 30 |
| Polysorbate 80 | 14 |
| Talcum powder | 5 |
| Titanium dioxide | 2 |
| 80% alcohol/aqueous solution | Appropriate |

The follows explains the preparation method of the double-layer controlled-release tablet of analgesic embodiments 1-5.

Analgesic Embodiment 1

1. Preparation of sustained-release granules:
   (1) Weigh ibuprofen sifted by a 60-mesh screen in accordance with the formula, hydroxypropylmethyl-cellose K100LV, K4M and lactose, mix them uniformly; then add silicon dioxide and magnesium stearate which are ½ of the dosages in the formula; and transfer the materials mixed to a wet type graulator.
   (2) Prepare the ethanol solution with concentration of 70% and prepare the soft material for the mixture in the first step.
   (3) Implement granulation for the soft material prepared by using a 24-mesh screen.
   (4) Dry and sifting the granules.
   (5) Acquiring the sustained-release granules for preparating the sustained-release layer.
2. Preparation of quick release granules:
   (1) Mix ketoprofen, lactose, microcrystalline cellulose, polyvidone in accordance with the formula and screen the mixture by using the 60-mesh screen; then add silicon dioxide and magnesium stearate, which are ½ of the dosages in the formula; and mix them uniformly in a mixer.
   (2) Prepare the ethanol solution with concentration of 80% and prepare the soft material for the mixture in the first step
   (3) Implement granulation for the soft material prepared by using a 24-mesh screen.
   (4) Dry and sifting the granules.
   (5) Add croscarmellose sodium in accordance with the extra-addition method and mix croscarmellose sodium and dry granules uniformly.
   (6) Acquiring the quick release granules, which for forming the quick release layer and filling the holes of the sustained-release layer.
3. Preparation of double-layer controlled-release tablet:
   (1) Press the granules of the sustained-release layer, the silicon dioxide and magnesium stearate left into the sustained-release tablets with holes in the middle, wherein the diameters are 3 mm, 4 mm and 6 mm, respectively. Moreover, press the sustained-release tablets without hole.
   (2) Put the sustained-release tablets into a punching die of a tablet press and fill the granules of quick-release layer; implement the second compressing in the way of shallow concave punching to form the double-layer tablets.
   (3) Disperse hydroxypropylmethyl-cellulose E5 in accordance with the formula in the ethanol with concentration of 80%; add polysorbate 80 after swelling; stir the mixture until the materials are dissolved completely and add titanium dioxide and talcum powder; then stir them uniformly and filter the mixture as the coating liquid.
   (4) Implement coating for the double-layer tablets, increasing the weight of each tablet for 5%, then dry and solidify the tablets.

The sustained-release layer should be pressed into the sustained-release tablets without hole, with holes having diameters 3 mm, with holes having diameters 4 mm and with holes having diameters 6 mm in this embodiment to implement the leaching test, in order to investigate effect of the hole diameter of the sustained-release layer for leaching, wherein the greater the hole diameter of the sustained-release layer is, the faster the leaching speed would be.

Figure 9:
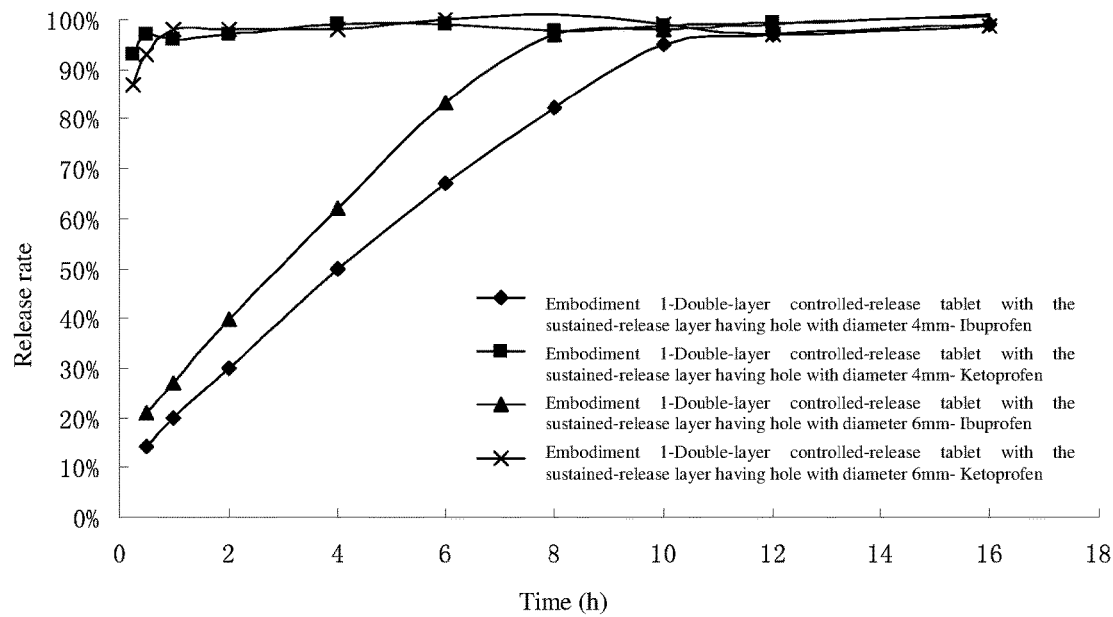
FIG. 9 is an in vitro release curve of the double-layer controlled-release tablet in analgesic embodiment 1.

The double-layer tablet prepared is applied to leaching test in order to investigate the sustained-release effect after quick release, wherein the quick release layer has been leached completely when sampling and detecting after 0.5 h, see FIG. 9 for the result. The zero-order effect is shown in the sustained-release layer, that is, the medicine is approximately released at constant speed. Moreover, the in vitro release at constant speed is useful for keeping the stable concentration of the patient; and it is worth mentioning that the greater the diameter of the hole of sustained-release layer, the faster the release speed would be.

Analgesic Embodiment 2

1. Preparation of sustained-release granules:
   (1) Weigh ibuprofen sifted by a 60-mesh screen in accordance with the formula, hydroxypropylmethyl-cellose K100LV, K4M and lactose, mix them uniformly; then add silicon dioxide and magnesium stearate which are ½ of the dosages in the formula; and transfer the materials mixed to a wet type granulator.
   (2) Prepare the ethanol solution with concentration of 75% and prepare the soft material for the mixture in the first step.
   (3) Implement granulation for the soft material prepared by using a 24-mesh screen.
   (4) Dry and sifting the granules.
   (5) Acquiring the sustained-release granules for preparing the sustained-release layer.
2. Preparation of quick release granules:
   (1) Mix naproxen, lactose, microcrystalline cellulose and hydroxy propyl cellulose-HF and sodium carboxymethylcellulose in accordance with the formula, screen by using the 60-mesh screen; then add silicon dioxide and magnesium stearate which are ½ of the dosages in the formula; and mix them uniformly in the mixer.
   (2) Prepare the ethanol solution with concentration of 90% and prepare the soft material for mixture in the first step
   (3) Implement granulation for the soft material prepared by using a 24-mesh screen.
   (4) Dry and sifting the granules.
   (5) Acquiring the quick release granules, which for forming the quick release layer and filling the holes of the sustained-release layer.
3. Preparation of double-layer controlled-release tablet:
   (1) Press the granules of the sustained-release layer, the silicon dioxide and magnesium stearate left into the sustained-release tablets with holes in the middle, wherein the diameters are 4 mm and 6 mm, respectively.
   (2) Put the sustained-release tablets into a punching die of a tablet press and fill the granules of quick-release layer; implement the second compressing in the way of shallow concave punching to form the double-layer tablets.
   (3) Disperse hydroxypropylmethyl-cellose E5 in accordance with the formula in the ethanol with concentration of 80%; add polysorbate 80 after swelling; stir the mixture until the materials are dissolved completely and add titanium dioxide and talcum powder; then stir them uniformly and filter the mixture as the coating liquid.
   (4) Implement coating for the double-layer tablets, increasing the weight of each tablet for 5 then dry and solidify the tablets.

Figure 10:
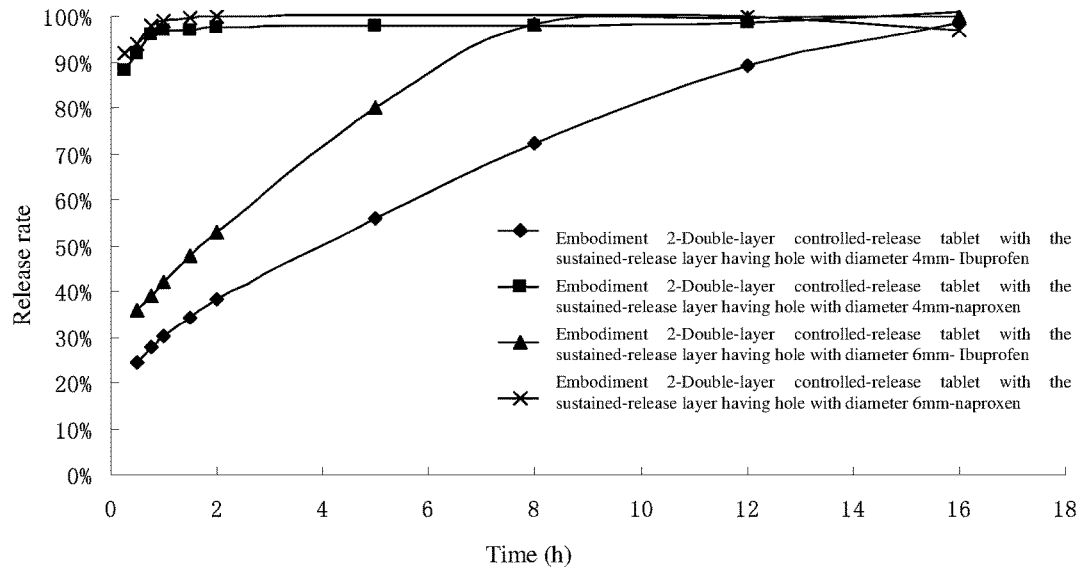
FIG. 10 is the in vitro release curve of the double-layer controlled-release tablet in analgesic embodiment 2.

Sampling and detection are implemented within 0.25 h in order to investigate the disintegrating speed of the quick release layer of the double-layer tablet and the sustained-release effect after quick release of the double-layer tablet, wherein the quick release layer is leached more than 85%; and see FIG. 10 for the result. The zero-order release effect is shown in the sustained-release layer, that is, the medicine is approximately released at constant speed. Moreover, the in vitro release at constant speed is useful for keeping the stable plasma concentration of the patient; and it is worth mentioning that the greater the diameter of the hole of the sustained-release layer, the faster the release speed would be.

Analgesic Embodiment 3

1. Preparation of sustained-release granules:
   (1) Weigh naproxen sifted by a 60-mesh screen in accordance with the formula, hydroxypropylmethyl-cellose K100LV, K4M and lactose, mix them uniformly; then add silicon dioxide and magnesium stearate which are ½ of the dosages in the formula; and transfer the materials mixed to a wet type granulator.
   (2) Prepare the ethanol solution with concentration of 80% and prepare the soft material for the mixture in the first step.
   (3) implement granulation for the soft material prepared by using a 24-mesh screen.
   (4) Dry and sifting the granules.
   (5) Acquiring the sustained-release granules for preparing the sustained-release layer.
2. Preparation of quick release granules:
   (1) Mix naproxen, lactose, microcrystalline cellulose and hydroxyl propyl cellulose-HF in accordance with the formula and screen the sodium carboxymethylcellulose by using the 60-mesh screen; then add silicon dioxide and magnesium stearate which are ½ of the dosages in the formula; and mix them uniformly in the mixer.
   (2) Prepare the ethanol solution with concentration of 90% and prepare the soft material for the mixture in the first step
   (3) Implement granulation for the soft material prepared by using a 24-mesh screen.
   (4) Dry and sifting the granules.
   (5) Acquiring the quick release granules, which for forming the quick release layer and filling the holes of the sustained-release layer.
3. Preparation of double-layer controlled-release tablet:
   (1) Press the granules of the sustained-release layer, the silicon dioxide and magnesium stearate into the sustained-release tablets with holes in the middle, wherein the diameters are 4 mm and 6 mm, respectively. Moreover, press the sustained-release tablets without hole.

(2) Put the sustained-release tablets into a punching die of a tablet press and fill the granules of quick-release layer; implement the second compressing in the way of shallow concave punching to form the double-layer tablets.

(3) Disperse hydroxypropylmethyl-cellose E5 in accordance with the formula in the ethanol with concentration of 80%; add polysorbate 80 after swelling; stir the mixture until the materials are dissolved completely and add titanium dioxide and talcum powder; then stir them uniformly and filter the mixture as the coating liquid.

(4) Implement coating for the double-layer tablets, increasing the weight of each tablet for 5%, then dry and solidify the tablets.

Figure 11:
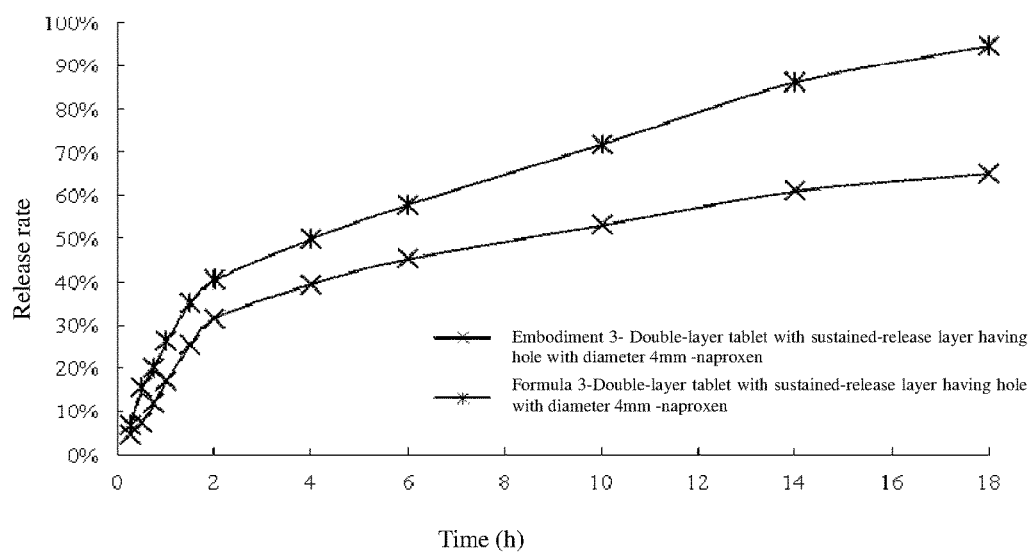
FIG. 11 is the leaching curve of the double-layer controlled-release tablet in analgesic 3.

The leaching tests are implemented for the double-layer tablet prepared in order to investigate the sustained-release effect after quick release of the tablet. Seen from the leaching curve, the quick release effect and sustained-release effect are significant; and see the FIG. 11 for the result.

Analgesic Embodiment 4

1. Preparation of sustained-release granules:
   (1) Weigh ibuprofen sifted by a 60-mesh screen in accordance with the formula, hydroxypropylmethyl-cellose K100LV, K4M and lactose, mix them uniformly; then add silicon dioxide and magnesium stearate which are ½ of the dosages in the formula; and transfer the materials mixed to a wet type granulator.
   (2) Prepare the ethanol solution with concentration of 70% and prepare the soft material for the mixture in the first step.
   (3) Implement granulation for the soft material prepared by using a 24-mesh screen.
   (4) Dry and sifting the granules.
   (5) Acquiring the sustained-release granules for preparing the sustained-release layer.
2. Preparation of quick release granules:
   (1) Mix ibuprofen, lactose, microcrystalline cellulose and hydroxy propyl cellulose-HF in accordance with the formula and screen the sodium carboxymethylcellulose by using the 60-mesh screen; then add silicon dioxide and magnesium stearate which are ½ of the dosages in the formula; and mix them uniformly in the mixer
   (2) Prepare the ethanol solution with concentration of 90% and prepare the soft material for mixture in the first step
   (3) implement granulation for the soft material prepared by using a 24-mesh screen.
   (4) Dry and sifting the granules.
   (5) Acquiring the quick release granules, which for forming the quick release layer and filling the holes of the sustained-release layer.
3. Preparation of double-layer controlled-release tablet:
   (1) Press the granules of the sustained-release layer, the silicon dioxide and magnesium stearate left into the sustained-release tablets with holes in the middle, wherein the diameters are 4 mm and 6 mm, respectively. Moreover, press the sustained-release tablets without hole.
   (2) Put the sustained-release tablets into a punching die of a tablet press and fill the granules of quick-release layer; implement the second compressing in the way of shallow concave punching to form the double-layer tablets.
   (3) Disperse hydroxyl propylmethyl-cellose E5 in accordance with the formula in the ethanol with concentration of 80%; add polysorbate 80 after swelling; stir the mixture until the materials are dissolved completely and add titanium dioxide and talcum powder; then stir them uniformly and filter the mixture as the coating liquid.
   (4) Implement coating for the double-layer tablets to increase the weight of each tablet for 5%, then dry and solidify the tablets.

Figure 12:
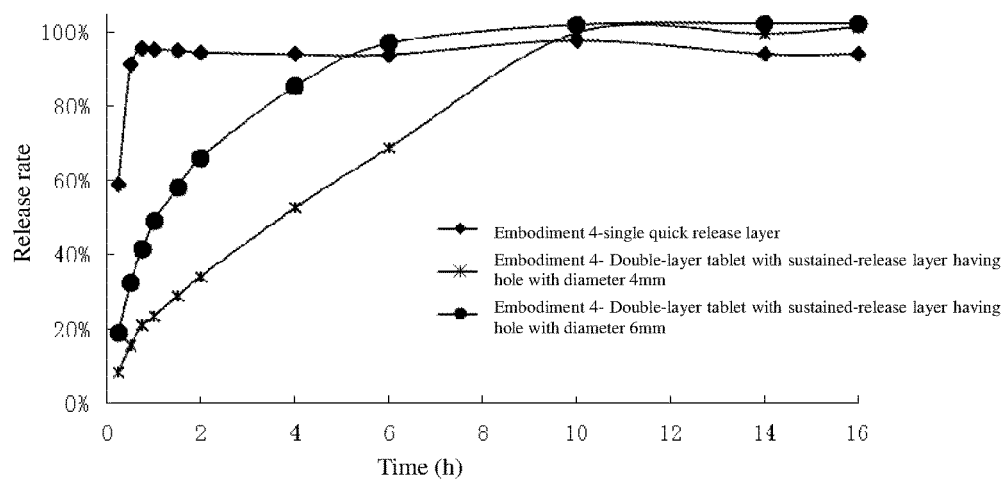
FIG. 12 is the leaching curve of the double-layer controlled-release tablet in analgesic embodiment 4.

The single-layer quick release tablet and the double-layer tablets are prepared to implement the leaching tests in order to investigate the disintegrating speed of the quick release layer of the and the effect of the hole diameter of the sustained-release layer to the sustained-release effect, wherein the quick release layer has been leached more than 90% when sampling and detecting after 0.5 h. Moreover, the linear effect of the in vitro leaching curve of the sustained-release layer having hole diameter of 4 mm is superior to the one of the in vitro leaching curve of the sustained-release layer having hole diameter of 6 mm in this embodiment; and see FIG. 12 for the result.

Analgesic Embodiment 5

The preparation method is the same as that in the embodiment 3, but the ingredients used are different, seeing the Table 1

The following shall explain the stability test of the analgesic double-layer tablet in the invention:
Test 1 Friability Test The inventor selected 100 double-layer tablets with the sustained-release layers without hole, 100 double-layer tablets with the sustained-release layers having holes with diameters of 3 mm, 4 mm or 6 mm respectively to implement the friability testing and comparison study by using the friability tester, the raw materials, the pharmaceutical excipients and the proportion were implemented in accordance with the embodiment 1; and see Table 2 for the result.

TABLE 2

Result of friability testing and comparison of double-layer tablet

| Type of the testing double-layer tablet | | Quantity of tablets subjected to breaking in 100 tablets | |
| --- | --- | --- | --- |
| Number of holes | Diameter of hole | Number of tablets broken | Number of tablets laminated |
| 0 | — | 20 | 11 |
| 1 | 6 mm | 9 | 0 |
| 1 | 4 mm | 1 | 0 |
| 1 | 3 mm | 1 | 0 |

It was proved from the result of said friability test that:
1) The occurrence rate of breaking of the double-layer tablets having holes in the invention was reduced greatly, and no lamination occurred.
2) The size of the diameter of the hole plays an active role in preventing lamination; but the of breaking of the double-layer tablet would be affected when the diameter of the hole is great.

Test 2 Effect of High Humidity to Stability of Medicine 20 double-layer tablets were selected from the embodiment 4 respectively, and were placed in the stability testing box to observe after 24 h, wherein the humidity was set at RH95%; and the temperature was set at 25° C. See Table 3 for the result.

TABLE 3

Effect of high humidity to stability of medicine

| Formula of the double-layer tablet | Type of testing double-layer tablet Number of | Diameter of hole | Number of tablets subjected to lamination among 100 tablets |
|---|---|---|---|
| In accordance with the embodiment 4 | 0 | — | 17 |
| | 1 | 6 mm | 0 |
| | 1 | 4 mm | 0 |
| | 1 | 3 mm | 0 |

The result indicated that the double-layer tablet of the invention still had nice stability and was not subjected to lamination under the condition that the ambient humidity was great, the swelling degree of the quick release layer was greater than that of the sustained-release layer and the double-layer tablet could not be separated easily although the quick release layer in the prescription included the super disintegrating agent, and the disintegrating agent had strong hygroscopicity.

Test 3 Effect of Number of Holes in Double-Layer Tablet to Stability

The double-layer tablets with sustained-release layers having no hole and the double-layer tablets having sustained-release layers with one, two and three holes were pressed in accordance with the formula in embodiment 3 (the quick release layer included only the active ingredients and excipient, but did not include the binder); 20 tablets were selected respectively to implement the friability tests in the friability tester and carry out comparison study; and see Table 4 for the result.

TABLE 4

Effect comparison of number of holes to stability

| Type of testing double-layer tablet | | Number of tablets | |
|---|---|---|---|
| Formula | Number of holes in the sustained-release layer | Number of tablets broken | subjected to lamination among 100 tablets Number of tablets laminated |
| In accordance with the embodiment 3 | 0 | 15 | 9 |
| | 1 | 6 | 0 |
| | 2 | 2 | 0 |
| | 3 | 1 | 0 |

It was proved by said friability test that:
1. The occurrence rate of breaking of the double-layer tablets having holes was reduced greatly, and no lamination occurred.
2. The number of the tablets broken would be reduced along increasing number of the holes.

See Table 5 for the prescription of the double-layer controlled-release tablet in hypnotic embodiments 1-5.

TABLE 5

| Component | Embodiment 1 | Embodiment 2 | Embodiment 3 | Embodiment 4 | Embodiment 5 |
|---|---|---|---|---|---|
| Sustained-release granules | | | | | |
| Zolpidem tartrate | 24 | 24 | / | / | / |
| Zopiclone | / | / | 30 | / | 36/ |
| Zaleplon | / | / | / | 30 | |
| Hydroxypropylmethyl-cellose K100lv | 30 | 60 | 105 | 0 | 90 |
| Hydroxypropylmethyl-cellose K4M | 60 | 30 | 0 | 105 | 15 |
| Lactose monohydrate | 183 | 183 | 159 | 159 | 156 |
| Silicon dioxide | 1.5 | 1.5 | 3 | 3 | 1.5 |
| Magnesium stearate | 1.5 | 1.5 | 3 | 3 | 1.5 |
| Total of sustained-release part | 300 | 300 | 300 | 300 | 300 |
| Quick release granules | | | | | |
| Zolpidem tartrate | 8 | 8 | / | / | / |
| Zopiclone | / | / | 5 | / | 10 |
| Zaleplon | / | / | / | 5 | / |
| Lactose | 57 | 55.5 | 60 | 60 | 55 |
| Microcrystalline cellulose | 25.5 | 25.5 | 31 | 25 | 25.5 |
| Polyvidone | 3.5 | 0 | 0 | 0 | 3.5 |
| Hydroxypropylmethyl-cellose -HF | 0 | 5 | 0 | 3 | 0 |
| Croscarmellose sodium | 4 | 4 | 2 | 6 | 5 |
| Silicon dioxide | 1 | 1 | 1 | 0.5 | 0.5 |
| Magnesium stearate | 1 | 1 | 1 | 0.5 | 0.5 |
| Total of quick release part | 100 | 100 | 100 | 100 | 100 |

The formula of the coating of the double-layer controlled-release tablet in hypnotic embodiments 1-5 is the same as that in said hypnotic embodiment.

The preparation method comprises steps of:

Hypnotic Embodiment

1. Preparation of sustained-release granules:
   ① Weigh zolpidem tartrate, hydroxypropylmethyl-cellose K100LV, K4M and lactose monohydrate sifted by the 60-mesh screen in accordance with the formula and mix them uniformly; then add silicon dioxide and magnesium stearate which are ½ of the dosages in the formula; and transfer the materials mixed to the wet type granulator.
   ② Prepare the ethanol solution with concentration of 70% and prepare the soft material for the mixture in the first step.
   ③ Implement granulation for the soft material prepared by using a 24-mesh screen.
   ④ Dry and sifting the granules.
   ⑤ Acquiring the sustained-release granules for preparing the sustained-release layer.
2. Preparation of quick release granules:
   ① Mix zolpidem tartrate, lactose, microcrystalline cellulose and polyvidone in accordance with the formula and screen the mixture by using the 60-mesh screen; then add silicon dioxide and magnesium stearate which are ½ of the dosages in the formula; and mix them uniformly in the mixer.
   ② Prepare the ethanol solution with concentration of 80% and prepare the soft material for the mixture in the first step
   ③ Implement granulation for the soft material prepared by using a 24-mesh screen.
   ④ Dry and sifting the granules.
   ⑤ Add croscarmellose sodium and dry granules in accordance with the extra-addition method and mix them uniformly.
   ⑥ Acquiring the quick release granules which for forming the quick release layer and filling the holes of the sustained-release layer.
3. Preparation of double-layer controlled-release tablet:
   ① Press the granules of the sustained-release layer, the silicon dioxide and magnesium stearate left into the sustained-release tablets with holes in the middle, wherein the diameters are 3 mm, 4 mm and 6 mm, respectively. Moreover, press the sustained-release tablets without hole.
   ② Put the sustained-release tablets into a punching die of a tablet press and fill the granules of quick-release layer; implement the second compressing in the way of shallow concave punching to form the double-layer tablets.
   ③ Disperse hydroxypropylmethyl-cellose E5 in accordance with the formula in the ethanol with concentration of 80%; add polysorbate 80 after swelling; stir the mixture until the materials are dissolved completely and add titanium dioxide and talcum powder; then stir them uniformly and filter the mixture as the coating liquid.
   ④ Implement coating for the double-layer tablets to increase the weight of each tablet for 5%, then dry and solidify the tablets.

Figure 4:
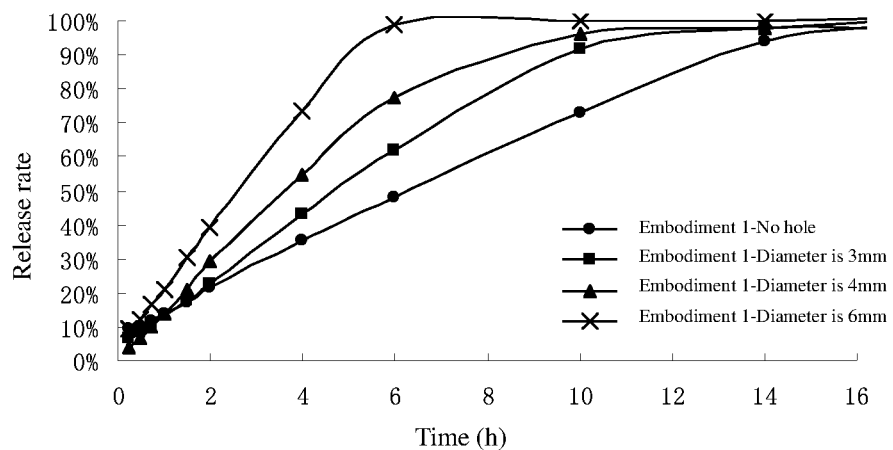
FIG. 4 is the leaching curve of the double-layer tablet in hypnotic embodiment 1 (wherein four curves indicate the table II-no hole available, table I having holes with diameters 3 mm, tablet having holes with diameters 4 mm and table I having holes with diameters 6 mm, respectively)

The sustained-release layer should be pressed into the sustained-release tablets without hole, with holes having diameters 3 mm, with holes having diameters 4 mm and with holes having diameters 6 mm in this embodiment to implement the leaching test, in order to investigate effect of the hole diameter of the sustained-release layer to leaching, wherein the greater the hole diameter of the sustained-release layer is, the faster the leaching speed would be. Moreover, see FIG. 4 for the result.

Figure 5:
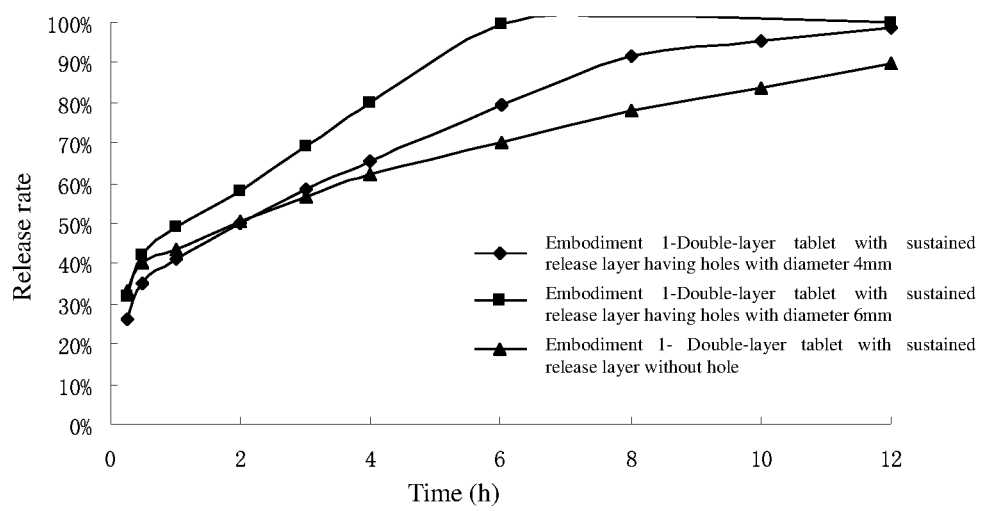
FIG. 5 indicates comparison of three leaching curves of the double-layer tablet having sustained-release layer with holes (diameters 4 mm and 6 mm) and the sustained-release layer with no hole available in hypnotic embodiment 1.

The double-layer tablet prepared is applied to leaching test in order to investigate the sustained-release effect after quick release, wherein the quick release layer has been leached completely when sampling and detecting after 0.5 h, see FIG. 5 for the result. See from the figure, the hole of the sustained-released layer can facilitate release at constant speed.

Hypnotic Embodiment 2

1. Preparation of sustained-release granules:
   ① Weigh zolpidem tartrate, hydroxypropylmethyl-cellose K100LV, K4M and lactose monohydrate sifted by the 60-mesh screen in accordance with the formula and mix them uniformly; then add silicon dioxide and magnesium stearate which are ½ of the dosages in the formula; and transfer the materials mixed to the wet type granulator.
   ② Prepare the ethanol solution with concentration of 75% and prepare the soft material for the mixture in the first step
   ③ Implement granulation for the soft material prepared by using a 24-mesh screen.
   ④ Dry and sifting the granules.
   ⑤ Acquiring the sustained-release granules for preparing the sustained-release layer.
2. Preparation of quick release granules:
   ① Mix zolpidem tartrate, lactose, microcrystalline cellulose and hydroxy propyl cellulose-HF in accordance with the formula and screen the sodium carboxymethylcellulose by using the 60-mesh screen; then add silicon dioxide and magnesium stearate which are ½ of the dosages in the formula; and mix them uniformly in the mixer.
   ② Prepare the ethanol solution with concentration of 90% and prepare the soft material for the mixture in the first step
   ③ Implement granulation for the soft material prepared by using a 24-mesh screen.
   ④ Dry and sifting the granules.
   ⑤ Acquiring the quick release granules which for forming the quick release layer and filling the holes of the sustained-release layer.
3. Preparation of double-layer controlled-release tablet:
   ① Press the granules of the sustained-release layer, the silicon dioxide and magnesium stearate left into the sustained-release tablets with holes in the middle, wherein the diameters are 4 mm and 6 mm, respectively. Moreover, press the sustained-release tablets without hole.
   ② Put the sustained-release tablets into a punching die of a tablet press and fill the granules of quick-release layer; implement the second compressing in the way of shallow concave punching to form the double-layer tablets.
   ③ Disperse hydroxypropylmethyl-cellose E5 in accordance with the formula in the ethanol with concentration of 80%; add polysorbate 80 after swelling; stir the mixture until the materials are dissolved completely and add titanium dioxide and talcum powder; then stir them uniformly and filter the mixture as the coating liquid.

④ Implement coating for the double-layer tablets to increase the weight of each tablet for 5%, then dry and solidify the tablets.

Figure 6:
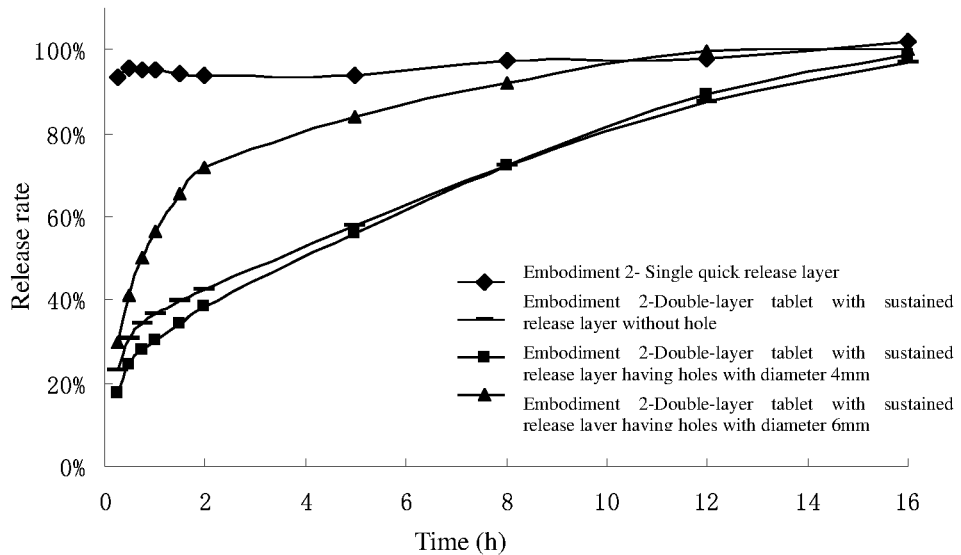
FIG. 6 indicates comparison of three leaching curves of the double-layer tablet having sustained-release layer with holes (diameters 4 mm and 6 mm) and the sustained-release layer with no hole available and only quick release layer in hypnotic embodiment 2.

The single-layer quick release tablet and the double-layer tablets are prepared to implement the leaching tests in order to investigate the disintegrating speed of the quick release layer of the medicine and the sustained-release effect after quick release of the double-layer tablet, wherein the quick release layer has been leached more than 90% when sampling and detecting after 0.25 h. Moreover, see FIG. 6 for the result.

Hypnotic Embodiment 3

1. Preparation of sustained-release granules:
   ① Weigh zopiclone, hydroxypropylmethyl-cellose K100LV, K4M and lactose sifted by the 60-mesh screen in accordance with the formula and mix them uniformly; then add silicon dioxide and magnesium stearate which are ½ of the dosages in the formula; and transfer the materials mixed to the wet type granulator.
   ② Prepare the ethanol solution with concentration of 80% and prepare the soft material for the mixture in the first step
   ③ Implement granulation for the soft material prepared by using a 24-mesh screen.
   ④ Dry and sifting the granules.)
   ⑤ (5) Acquiring the sustained-release granules for preparing the sustained-release layer.
2. Preparation of quick release granules:
   ① Mix zopiclone, lactose, microcrystalline cellulose and hydroxy propyl cellulose-HF in accordance with the formula and screen the sodium carboxymethylcellulose by using the 60-mesh screen; then add silicon dioxide and magnesium stearate which are ½ of the dosages in the formula; and mix them uniformly in the mixer.
   ② Prepare the ethanol solution with concentration of 90% and prepare the soft material for the mixture in the first step
   ③ Implement granulation for the soft material prepared by using a 24-mesh screen.
   ④ Dry and sifting the granules.
   ⑤ Form the quick release layer and fill the holes of the sustained-release layer after acquiring the
3. Preparation of double-layer controlled-release tablet:
   ① Press the granules of the sustained-release layer, the silicon dioxide and magnesium stearate left into the sustained-release tablets with holes in the middle, wherein the diameters are 4 mm and 6 mm, respectively. Moreover, press the sustained-release tablets without hole.
   ② Put the sustained-release tablets into a punching die of a tablet press and fill the granules of quick-release layer; implement the second compressing in the way of shallow concave punching to form the double-layer tablets.
   ③ Disperse hydroxypropylmethyl-cellose E5 in accordance with the formula in the ethanol with concentration of 80%; add polysorbate 80 after swelling; stir the mixture until the materials are dissolved completely and add titanium dioxide and talcum powder; then stir them uniformly and filter the mixture as the coating liquid.
   ④ Implement coating for the double-layer tablets to increase the weight of each tablet for 5%, dry and solidify the tablets.

Figure 7:
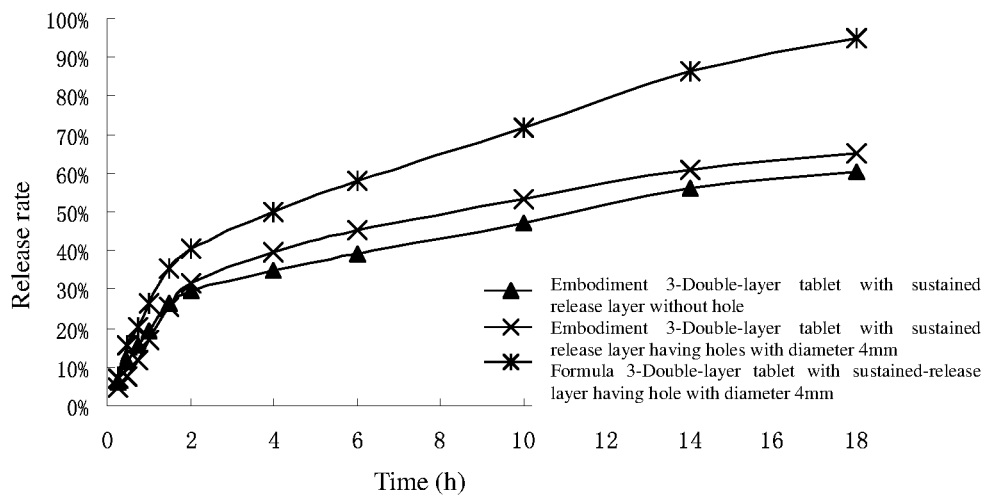
FIG. 7 indicates comparison of three leaching curves of the double-layer tablet having sustained-release layer with holes (diameters 4 mm and 6 mm) and the sustained-release layer with no hole available in hypnotic embodiment 3.

The double-layer tablets prepared are applied to leaching test in order to investigate the sustained-release effect after quick release of the tablet; the quick release layer has been leached completely when sampling and detecting after 0.5 h. Moreover, see FIG. 7 for the result.

Hypnotic Embodiment 4

1. Preparation of sustained-release granules:
   ① Weigh zaleplon, hydroxypropylmethyl-cellose K100LV, K4M and lactose sifted by the 60-mesh screen in accordance with the formula and mix them uniformly; then add silicon dioxide and magnesium stearate which are ½ of the dosages in the formula; and transfer the materials mixed to the wet type granulator.
   ② Prepare the ethanol solution with concentration of 80% and prepare the soft material for the mixture in the first step
   ③ Implement granulation for the soft material prepared by using a 24-mesh screen.
   ④ Dry and sifting the granules.
   ⑤ (5) Acquiring the sustained-release granules for preparing the sustained-release layer.
2. Preparation of quick release granules:
   ① Mix zaleplon, lactose, microcrystalline cellulose and hydroxy propyl cellulose-HF in accordance with the formula and screen the sodium carboxymethylcellulose by using the 60-mesh screen; then add silicon dioxide and magnesium stearate which are ½ of the dosages in the formula; and mix them uniformly in the mixer.
   ② Prepare the ethanol solution with concentration of 90% and prepare the soft material for the mixture in the first step
   ③ Implement granulation for the soft material prepared by using a 24-mesh screen.
   ④ Dry and sifting the granules.
   ⑤ Form the quick release layer and fill the holes of the sustained-release layer after acquiring the
3. Preparation of double-layer controlled-release tablet:
   ① Press the granules of the sustained-release layer, the silicon dioxide and magnesium stearate left into the sustained-release tablets with holes in the middle, wherein the diameters are 4 mm and 6 mm, respectively. Moreover, press the sustained-release tablets without hole.
   ② Put the sustained-release tablets into a punching die of a tablet press and fill the granules of quick-release layer; implement the second compressing in the way of shallow concave punching to form the double-layer tablets.
   ③ Disperse hydroxypropylmethyl-cellose E5 in accordance with the formula in the ethanol with concentration of 80%; add polysorbate 80 after swelling; stir the mixture until the materials are dissolved completely and add titanium dioxide and talcum powder; then stir them uniformly and filter the mixture as the coating liquid.
   ④ Implement coating for the double-layer tablets to increase the weight of each tablet for 5%, then dry and solidify the tablets.

Figure 8:
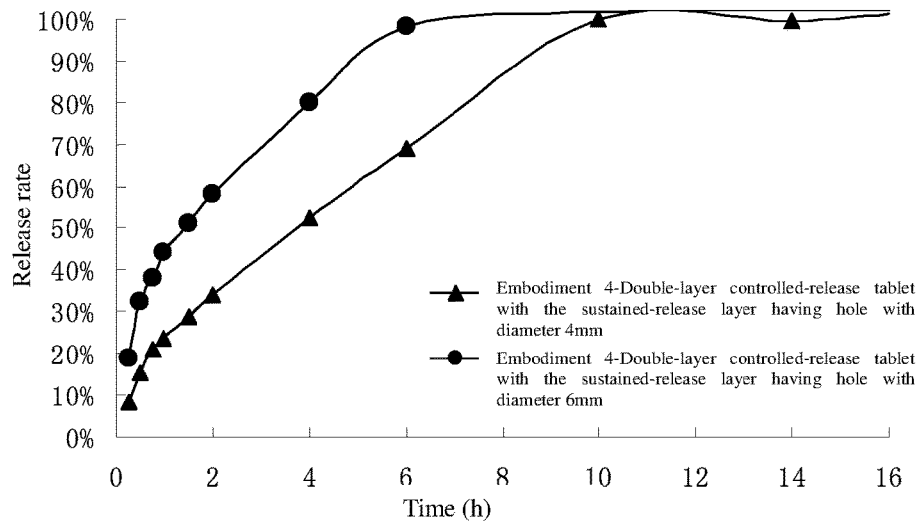
FIG. 8 indicates comparison of two leaching curves of the double-layer tablet having sustained-release layer with holes (diameters 4 mm and 6 mm) and the sustained-release layer with no hole available in hypnotic embodiment 4.

The single-layer quick release tablet and the double-layer tablets are prepared to implement the leaching tests in order to investigate the disintegrating speed of the quick release layer of the medicine and the sustained-release effect after quick release of the double-layer tablet, wherein the quick release layer has been leached more than 90% when sampling and detecting after 0.25 h. Moreover, see FIG. 8 for the result.

Hypnotic Embodiment 5

The preparation method is the same as that in the embodiment 3, but the ingredients to be used are different, seeing the Table 1
Friability Test and Stability Test of Hypnotic Tablet 100 double-layer tablets having sustained-release layer without hole and 100 double-layer tablets having sustained-release layer with holes of different diameters are prepared respectively in accordance with the formula and the method in the embodiment 1 in order to implement friability testing and comparison study in the friability tester respectively; and see Table 6 for the result.

TABLE 6

| Testing object | | Number of tablets broken | Number of tablets laminated |
|---|---|---|---|
| | Drilling condition of sustained-release layer | | |
| Double-layer tablet in accordance with the formula in embodiment 1 | Without hole | 12 | 8 |
| | Hole with diameter of | 4 | 0 |
| | Hole with diameter of | 1 | 0 |
| | Hole with diameter of | 1 | 0 |

The result indicates that:
1. The double-layer tablets with sustained-release layer having holes are not subjected to lamination.
2. The tablets having small diameters would less likely to be broken.

20 double-layer tablets with sustained-release layer having no hole and 20 double-layer tablets with sustained-release layers having holes of different diameters were prepared in accordance with the formula and method in the embodiment 4 respectively, and were placed in the stability testing box, wherein the humidity was set at RH95%; and the temperature was set at 25° C.

Observe the double-layer tablets after 24 h, and see Table 7 for the result.

TABLE 7

| Testing object | | Number of tablets laminated |
|---|---|---|
| | Drilling condition of sustained-release layer | |
| Double-layer tablets in accordance with the formula in embodiment 4 | Without hole | 17 |
| | Hole with diameter of 6 mm | 0 |
| | Hole with diameter of 4 mm | 0 |
| | Hole with diameter of 3 mm | 0 |

The quick release layer of the formula includes the super disintegrating agent having strong hygroscopicity; the degree of swelling of the quick release layer is greater than that of the sustained-release layer, and upper layer and the lower layer of the double-layer tablet without hole may be separated from each other when the ambient humidity is great. The quick release granules in the hole may swell after absorbing the moisture when the sustained-release layer has the hole, and quick release layer may be combined with the sustained-release layer more tightly. Therefore, the double-layer tablet having hole is not subjected to separation during the test.

The result indicated that the double-layer tablet of the invention could keep the stability in the high-temperature and high-humidity environment.

20 double-layer tablets with sustained-release layer having no hole and 20 double-layer tablets with sustained-release layers having different number of holes were prepared in accordance with the formula and method in the embodiment 3 respectively, and were placed in the friability tester to carry out the friability testing and comparison study, wherein the quick release layer included only the active ingredients and the excipient, but did not include the binder. Moreover, see Table 8 for the result.

TABLE 8

| Testing object | | | |
|---|---|---|---|
| | Drilling condition of sustained-release layer | Number of tablets broken | Number of tablets laminated |
| Double-layer tablets in accordance with the formula in embodiment 3 | 0 | 15 | 9 |
| | 1 | 6 | 0 |
| | 2 | 2 | 0 |
| | 3 | 1 | 0 |

The result indicates that:
1 The double-layer tablets with sustained-release layer having holes are not subjected to lamination.
2. The double-layer tablets having more holes would less likely to be broken.

Seen from the above-mentioned result, the double-layer tablet prepared in the invention has the physical stability superior to the common double-layer tablet, and is more useful for storage and transportation; further, the medicine in the double-layer tablet can be released approximately at constant speed.

The invention claimed is:
1. A method of preparing a double-layer tablet comprising an upper layer on top of a lower layer, comprising:
　1) pressing a first active ingredient and a first pharmaceutically acceptable excipient to form the upper layer, wherein the upper layer is a sustained-release layer and comprises one or more holes, and the diameter of each hole is between about 2 mm and about 6 mm; and
　2) pressing the upper layer onto a second active ingredient and a second pharmaceutically acceptable excipient, which are configured to form the lower layer, to form the double-layer tablet comprising the upper layer on top of the lower layer,
　thereby part of the second active ingredient and the second pharmaceutically acceptable excipient of the lower layer are filled into the hole(s) of the upper layer.
2. The method of claim 1, wherein the first and second active ingredients are the same or different from each other.
3. The method of claim 1, wherein the first and second pharmaceutically acceptable excipients are selected from the group consisting of: a sustained-release material, a filler, a disintegrating agent, a lubricant, a binder, a glidant, and any combination thereof.
4. The method of claim 3, wherein:
　the sustained-release material is selected from the group consisting of: hydroxylpropyl methylcellulose, ethyecellulose, hydroxypropyl cellulose, and any combination thereof;
　the filler is selected from the group consisting of: lactose, pregelatinized starch, microcrystalline cellulose, and any combination thereof;

the disintegrating agent is selected from the group consisting of: sodium carboxymethyl cellulose, sodium carboxymethyl starch, polyvinylpolypyrrolidone, and any combination thereof;
the lubricant is selected from the group consisting of: stearic acid, magnesium stearate, talcum powder, and any combination thereof;
the binder is selected from the group consisting of: polyvidone, hydroxy propyl cellulose, hydroxylpropyl methylcellulose, and any combination thereof; and
the glidant is fine silica powder.

5. The method of claim 1, wherein:
the tablet is a controlled-release tablet,
the upper layer is a sustained-release layer comprising the first active ingredient, a sustained-release material, and the first pharmaceutically acceptable excipient; the first active ingredient has a hypnotic effect; the sustained-release layer comprises one or more holes which are filled with rapid-release granules; and the diameter of each hole is between about 3 mm and about 6 mm,
the lower layer is a rapid-release layer comprising the rapid-release granules comprising: the second active ingredient which has a hypnotic effect and the second pharmaceutically acceptable excipient, and
the controlled-release tablet is manufactured using a method comprising:
1) mixing the first active ingredient, the sustained-release material, and the first pharmaceutically acceptable excipient to form sustained-release granules, and
mixing the second active ingredient and the second pharmaceutically acceptable excipient to form the rapid-release granules;
2) pressing the sustained-release granules to form the sustained-release layer comprising one or more holes, placing the sustained-release layer into a die of a tablet press, filling the die with the rapid-release granules, and pressing the sustained-release layer onto the rapid-release granules, thereby filling the hole(s) of the sustained-release layer with the rapid-release granules to form the controlled-release tablet.

6. The method of claim 5, wherein:
the first and second active ingredients are selected from the group consisting of: zolpidem, zaleplon, zopiclone, triazolam, midazolam, flurazepam, diazepam, chlordiazepoxide, nitrazepam, estazolam, alprazolam, lorazepam, and any combination thereof;
the sustained-release material is selected from the group consisting of: hydroxylpropyl methylcellulose, ethyecellulose, hydroxypropyl cellulose, and any combination thereof; and
the first and second pharmaceutically acceptable excipients are selected from the group consisting of: a filler, a disintegrating agent, a lubricant, a binder, a glidant, and any combination thereof.

7. The method of claim 6, wherein:
the filler is selected from the group consisting of: lactose monohydrate, lactose, pregelatinized starch, microcrystalline cellulose, and any combination thereof;
the disintegrating agent is selected from the group consisting of: sodium carboxymethyl cellulose, croscarmellose sodium, sodium carboxymethyl starch, polyvinylpolypyrrolidone, and any combination thereof;
the lubricant is selected from the group consisting of: stearic acid, magnesium stearate, talcum powder, and any combination thereof;
the binder is selected from the group consisting of: polyvidone, hydroxy propyl cellulose, hydroxylpropyl methylcellulose, and any combination thereof; and
the glidant is silicon dioxide.

8. The method of claim 5, wherein:
the sustained-release layer comprises the following components in weight percentage:

| | |
|---|---|
| the first active ingredient: | 8-12%, |
| the sustained-release material: | 30-35%, |
| the filler: | 52-61%, |
| the lubricant: | 0.5% or 1%, and |
| the glidant: | 0.5% or 1%; and | the rapid-release layer and rapid-release granules comprise the following components in weight percentage:

| | |
|---|---|
| the second active ingredient: | 5-10%, |
| the disintegrating agent: | 2-6%, |
| the filler: | 80.5-91%, |
| the binder: | 0-5%, |
| the lubricant: | 0.5% or 1%, and |
| the glidant: | 0.5% or 1%. |

9. The method of claim 5, further comprising a step of coating the tablet with a coating layer comprising the following components in weight percentage, in 80% alcohol in water as a solvent:

| | |
|---|---|
| hydroxypropyl methylcellulose E5: | 30%, |
| Polysorbate 80: | 14%, |
| talcum powder: | 5%, and |
| titanium dioxide: | 2%. |

10. The method of claim 1, wherein:
the tablet is a controlled-release tablet,
the upper layer is a sustained-release layer comprising the first active ingredient, a sustained-release material, and the first pharmaceutically acceptable excipient; the first active ingredient has an analgesic effect; the sustained-release layer comprises one or more holes which are filled with rapid-release granules; and the diameter of each hole is between about 3 mm and about 6 mm,
the lower layer is a rapid-release layer comprising the rapid-release granules comprising: the second active ingredient which has an analgesic effect and the second pharmaceutically acceptable excipient, and
the controlled-release tablet is manufactured using a method comprising:
1) mixing the first active ingredient, the sustained-release material, and the first pharmaceutically acceptable excipient to form sustained-release granules, and
mixing the second active ingredient and the second pharmaceutically acceptable excipient to form the rapid-release granules;
2) pressing the sustained-release granules to form the sustained-release layer comprising one or more holes, placing the sustained-release layer into a die of a tablet press, filling the die with the rapid-release granules, and pressing the sustained-release layer onto the rapid-release granules, thereby filling the hole(s) of the sustained-release layer with the rapid-release granules to form the controlled-release tablet.

11. The method of claim 10, wherein:
the first and second active ingredients are selected from the group consisting of: aspirin, magnesium salicylate, sodium salicylate, choline magnesium trisalicylate, diflunisal, salsalate, ibuprofen, indometacin, flurbiprofen, phenoxy ibuprofen naproxen, nabumetone, piroxicam, phenylbutazone, diclofenac sodium, fenoprofen, ketoprofen, ketorolac, tetraclofenamic acid, sulindac, tolmetin, anisodamine, and any combination thereof;
the sustained-release material is selected from the group consisting of: hydroxylpropyl methylcellulose, ethyecellulose, hydroxypropyl cellulose, and any combination thereof; and
the first and second pharmaceutically acceptable excipients are selected from the group consisting of: a filler, a disintegrating agent, a lubricant, a binder, a glidant, and any combination thereof.

12. The method of claim 11, wherein:
the filler is selected from the group consisting of: lactose monohydrate, lactose, pregelatinized starch, microcrystalline cellulose, and any combination thereof;
the disintegrating agent is selected from the group consisting of: sodium carboxymethyl cellulose, croscarmellose sodium, sodium carboxymethyl starch, polyvinylpolypyrrolidone, and any combination thereof;
the lubricant is selected from the group consisting of: stearic acid, magnesium stearate, talcum powder, and any combination thereof;
the binder is selected from the group consisting of: polyvidone, hydroxy propyl cellulose, hydroxylpropyl methylcellulose, and any combination thereof; and
the glidant is silicon dioxide.

13. The method of claim 10, wherein:
the sustained-release layer comprises the following components in weight percentage:

| | |
|---|---|
| the first active ingredient: | 40-60%, |
| the sustained-release material: | 25-35%, |
| the filler: | 13-24%, |
| the lubricant: | 0.5% or 1%, and |
| the glidant: | 0.5% or 1%; and | the rapid-release layer and rapid-release granules comprise the following components in weight percentage:

| | |
|---|---|
| the second active ingredient: | 30-60%, |
| the disintegrating agent: | 3-6%, |
| the filler: | 30-60.5%, |
| the binder: | 0-5%, |
| the lubricant: | 0.5% or 1%, and |
| the glidant: | 0.5% or 1%. |

14. The method of claim 10, further comprising a step of coating the tablet with a coating layer comprising the following components in weight percentage, in 80% alcohol in water as a solvent:

| | |
|---|---|
| hydroxypropyl methylcellulose E5: | 30%, |
| Polysorbate 80: | 14%, |
| talcum powder: | 5%, and |
| titanium dioxide: | 2%. |

* * * * *